United States Patent [19]

Lazar et al.

[11] Patent Number: 5,155,120
[45] Date of Patent: Oct. 13, 1992

[54] METHOD FOR TREATING CONGESTIVE HEART FAILURE

[75] Inventors: Jeffrey D. Lazar; Joseph F. Souhrada; Svetislav K. Vanov, all of Groton, Conn.

[73] Assignee: Pfizer Inc, New York, N.Y.

[21] Appl. No.: 767,173

[22] Filed: Sep. 27, 1991

Related U.S. Application Data

[63] Continuation of Ser. No. 650,838, Jan. 14, 1991, abandoned.

[51] Int. Cl.$^5$ ............................................. A01N 43/40
[52] U.S. Cl. ..................................................... 514/356
[58] Field of Search .......................................... 514/356

[56] References Cited

PUBLICATIONS

Dunselman et al, "Efficacy of Felodipine in Congestive Heart Failure," Eur; Heart J. 10:354-364 1989.
Packer, "Calcium Channel Blockers in Chronic Heart Failure" Circulation 82:2254-2257 1990.

*Primary Examiner*—Frederick E. Waddell
*Assistant Examiner*—Gregory Hook
*Attorney, Agent, or Firm*—Peter C. Richardson; J. Trevor Lumb; James M. McManus

[57] ABSTRACT

Method for the treatment of congestive heart failure using amlodipine and the pharmaceutically acceptable acid addition salts thereof.

3 Claims, No Drawings

METHOD FOR TREATING CONGESTIVE HEART FAILURE

CROSS-REFERENCE TO RELATED APPLICATIONS

This application is a continuation application of copending application Ser. No. 07/650,838, filed Jan. 14, 1991, now abandoned.

BACKGROUND OF THE INVENTION

1. Field of the Invention

This invention relates to the antihypertensive agent amlodipine and its pharmaceutically acceptable acid addition salts and their use in treating congestive heart failure.

2. Description of the Prior Art

Congestive heart failure, regardless of its etiology, is characterized by a weakness of the myocardial tissue of the left and/or right ventricles of the heart to pump and circulate blood into systemic and/or pulmonary circulations. It is accompanied by circulatory and neurohumoral changes which result in failure to deliver sufficient blood and oxygen supply to peripheral tissues and vital organs. If left untreated the health of a patient with congestive heart failure could deteriorate to the point where the disease would be fatal.

While there are several therapies available for the treatment of congestive heart failure, the most widely used is digitalis. Its use is limited because of its slow onset of action and the small difference between the maximum therapeutic and minimum toxic dose levels.

SUMMARY OF THE INVENTION

A therapy has now been found for treating congestive heart failure in a human subject having such condition which comprises orally or parenterally administering to said human subject a congestive heart failure treating amount of amlodipine and the pharmaceutically acceptable acid addition salts thereof. It is preferred that the daily dosage be given in unit dosage form of 10 mg once a day orally.

While amlodipine belongs to a family of calcium channel blockers useful as antihypertensive and in the treatment of ischemic heart disease such agents are considered ineffective in treating congestive heart disease and may be deleterious if administered to a patient in heart failure. Consequently, the discovery that amlodipine is useful in treating congestive heart failure is unexpected.

DETAILED DESCRIPTION OF THE INVENTION

As previously mentioned, the antihypertensive compound of the present method invention is known in the art. Amlodipine, 3-ethyl-5-methyl 2-(2-aminoethoxymethyl)-4-(2-chlorophenyl)-1,4-dihydro-6-methylpyridine-3,5-dicarboxylate, and its pharmaceutically acceptable acid addition salts are claimed and their preparation described in U.S. Pat. Nos. 4,572,909 and 4,879,303. The chemical structure of amlodipine is as follows:

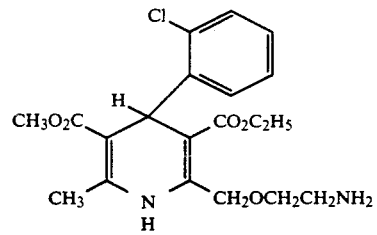

p Although the generic name of amlodipine represents the free base, the present method invention is meant to embrace pharmaceutically acceptable acid addition salts, such as hydrochloride, hydrobromide, hydroiodide, nitrate, sulfate, bisulfate, phosphate, acid phosphate, acetate, lactate, citrate, acid citrate, tartrate, bitartrate, succinate, maleate, gluconate, methanesulfate, ethanesulfate, benzenesulfonate and p-toluenesulfonate salts.

In the treatment of congestive heart failure it is generally preferred to administer amlodipine or its pharmaceutically acceptable acid addition salts orally once a day. In using amlodipine or one of its pharmaceutically acceptable acid addition salts in congestive heart failure, a dosage level of 5 mg to 20 mg per day is therapeutically effective, and a preferred dose is 10 mg per day.

It is to be appreciated that still other variations may also occur in this respect, depending upon the individual response to said medicament, as well as on the particular type of pharmaceutical formulation chosen and the time period and interval at which such administration is carried out. In some instances, dosage levels below the lower limit of the aforesaid range may be more than adequate, while in other cases still larger dosages may be employed without causing any harmful or deleterious side effects to occur provided that such higher dose levels are first divided into several smaller doses that are to be administered throughout the day. Amlodipine can be given alone or in combination with digitalis, thiazide diuretics, other diuretics, ACE inhibitors, etc.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidine, sucrose, gelatin and acacia. Additionally, lubricating agents such as magnesium stearate, sodium lauryl sulfate and talc are often very useful for tableting purposes. Solid compositions of a similar type may also be employed as fillers in soft elastic and hard-filled gelatin capsules; preferred materials in this connection also include lactose or milk sugar as well as high molecular weight polyethylene glycols. When aqueous suspension and/or elixirs are desired for oral administration, the essential active ingredient may be combined with various sweetening or flavoring agents, coloring matter or dyes and, if so desired, emulsifying and/or suspending agents, together with such diluents as water, ethanol, propylene glycol, glycerin and various like combinations thereof.

Although the preferred mode of administration of amlodipine or one of its pharmaceutically acceptable acid addition salts is oral, they may be administered parenterally as well.

For purposes of parenteral administration, solutions of amlodipine in sesame or peanut oil or in aqueous-propylene glycol may be employed, as well as sterile aqueous solutions of the corresponding water-soluble acid addition salts previously enumerated. Such aqueous solutions should be suitably buffered if necessary and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter, such as a sintered-glass filter or a diatomaceous-earth or unglazed porcelain filter. Preferred filters of this type include the Berkefeld, the Chamberland and the asbestos disc-metal Seitz filter, wherein the fluid is sucked through the filter candle into a sterile container with the aid of a suction pump. The necessary steps should be taken throughout the preparation of these injectable solutions to ensure that the final products are obtained in a sterile condition.

The following examples are provided solely for the purpose of illustration and are not to be construed as limitations of this invention, many variations of which are possible without departing from the spirit or scope thereof. The clinical studies which comprise the following example were conducted with amlodipine benzenesulfonate.

EXAMPLE

I. Purpose of Study

The purpose of the study was to evaluate the efficacy of fixed doses amlodipine tablets (10 mg/day) compared with placebo in the chronic treatment (8 wks) of patients with significantly compromised left ventricular function.

II. Trial Design

This was a randomized, parallel, double-blind, placebo-controlled study of amlodipine in outpatients with NYHA functional class IIM-III chronic heart failure. The duration of this study was 10 weeks; a 2 week single-blind placebo phase was followed by an 8 week double-blind phase during which patients received either placebo or amlodipine. The study consisted of three phases:
(1) stabilization and screening phase.
(2) single-blind phase.
(3) double-blind phase.

Stabilization and Screening Phase

Prior to entry into the study, the patient had to meet the following criteria:
1) patient body weight had to be stable (±4 pounds) for at least two weeks;
2) in patients on ACE inhibitors, therapeutic regimen had to be constant for 12 weeks;
3) therapeutic regimens with digitalis and diuretics had to be constant for at least four weeks;
4) therapy which was specifically listed in exclusion criteria had to be discontinued for at least two weeks.

Upon meeting these criteria, patients underwent baseline screening which included clinical evaluation, one treadmill exercise test, a chest X-ray, laboratory safety tests, and determination of left ventricular ejection fraction. In several centers, patients had radionuclide angiographic studies using the multiple gated equilibrium cardiac blood-pool imaging technique (at rest and optionally on exercise). The use of two dimensional and Doppler echocardiography was optional. Once the screening visit was completed, patients entered the single-blind phase of study.

Single-blind Outpatient Phase

During the single-blind outpatient phase, all patients had to complete 2 consecutive treadmill tests with total exercise time within 15% of one another. One additional exercise test was allowed if the duration of the two previous tests were not within 15%. However, in order to qualify for continuation in this study, exercise tests took place within the time period of 14-28 days (single-blind placebo phase). After the last exercise test was completed, 24-hour Holter ECG monitoring was performed on those patients who qualified for randomization.

Double-blind Outpatient Phase

After the single-blind phase, patients who qualified were randomized into the double-blind outpatient phase (8 week duration). Patients were allocated to treatments by means of computer generated randomized lists. The assignment was stratified by the presence or absence of ACE inhibitor therapy. Drug was provided for the two groups identified as "ACE Inhibitors"; and "No ACE Inhibitors," respectively.

The patients were evaluated at the end of study weeks 4, 6, 8 and 10 (2, 4, 6, and 8 weeks of double-blind treatment). At each clinic visit, a sitting blood pressure, pulse rate, and body weight was determined. A 12-lead ECG, treadmill exercise test, and a 24 hour Holter ECG monitoring was performed at the end of study weeks 6 and 10. Radionuclide angiography, two dimensional, and Doppler echocardiography (these two tests were optional and were done in selected centers), and chest X-ray were performed at the end of week 10.

Additional Optional Parameters

At the end of weeks 2 and 10 of the study, 50 ml of blood was collected for optional determination of cardiorenal hormones. Determination of gated radionuclide ventriculography at rest and during exercises was done at screening and at the end of week 10.

III. Subject Selection Criteria

A. Inclusion in Study

1. Age 21-80 years.
2. Males, or non-pregnant, non-lactating or postmenopausal females.
3 Outpatients.
4 Medical history and physical examination before inclusion in the study.
5. Written informed consent from the patient to participate in the study.
6. Diagnostic criteria, each of the following:
   a) clinical diagnosis of congestive heart failure.
   b) objective evidence of CHF, present for at least 6 weeks detected by: left ventricular ejection fraction of 0.40 or less at rest (as measured by radionuclide angiography or contrast ventriculography) and,
   c) New York Heart Association functional class IIM to III.
7. Etiology of heart failure to be:
   a) Ischemic heart disease,
   b) Myocardial disease of known or unknown cause.

8. All patients to be in stable clinical condition and could receive concomitant therapy with furosemide and a digitalis preparation, ACE inhibitors and/or vasodilators such as intermittent therapy with sublingual nitroglycerine. However, ACE inhibitor dosages must have been constant for at least 12 weeks. Sublingual nitroglycerin p.r.n. was allowed for angina attack relief.

9. Patients must be capable of undertaking a treadmill exercise test using the modified Naughton protocol and have a duration of at least 2 minutes but less than 16 minutes.

IV. Clinical Observation and Laboratory Measurements

A. Efficacy

Effect of amlodipine treatment on efficacy parameters was evaluated as follows:

1. Symptom Rating: At each visit patients received a detailed cardiopulmonary assessment of symptoms (dyspnea, fatigue, orthopnea, paroxysmal nocturnal and clinical dyspnea and edema) signs including lung congestion and ankle and pedal edema graded on a 4 point scale in absolute terms.

2. Patient Self-Assessment (Quality of Life Questionnaire): At each review visit, patients completed the self-assessment analysis of symptoms questionnaire (graded on a "thermometer scale" and exercise capabilities duration of a fixed pattern of activity) recorded at screening, at the end of single-blind period, after 4 weeks of double-blind therapy and at the end of double-blind therapy.

3. Global Evaluation: The investigator determined a global graded estimate of the patient's condition at each review visit and at the end of the double-blind therapy.

4. The following parameters were measured at baseline, at the end of 2 weeks single-blind therapy, after 4 weeks of double-blind therapy, and at the end of 8 weeks of double-blind therapy.
   a) 24-hour Holter monitoring;
   b) Standard 12-lead ECG immediately prior to each exercise test;
   c) Exercise tolerance (duration) as measured by treadmill exercise testing using the modified Naughton protocol. Optional measurement of oxygen consumption at peak exercise was also included.
   d) In selected centers, resting radionuclide imaging left ventricular ejection fraction was performed at screening and at the end of the double-blind phase (10th week of study). There was an optional determination of two-dimensional echocardiography and Doppler echocardiography and measurement of cardiorenal hormones in selected centers.

V. Statistical Methodology

Baseline for total exercise time was defined as the mean recorded time (in secs) of the last 2 exercise tests during the single-blind placebo phase. The baseline LVEF was at the screening visit. Baseline for ECG, body weight and norepinephrine was at week 2.

The statistical analyses for efficacy parameters were carried out on two subsets of patients corresponding to two definitions of study "end";

1) Final-baseline Analysis: All patients who completed the study are included in this subset. For the total exercise time, patients also have to satisfy the "reproducible" criterion for their exercise test. That is, the two consecutive treadmill tests have to be within 120 to 900 seconds and within 15% of one another.

2) Intent to Treat Analysis: All patients who had efficacy measurements collected during the double-blind treatment period were included for this analysis.

The comparison between treatment groups for the above mentioned parameters were based on the difference in the log (base e) scale; i.e., the log change is defined as:

$$c = ln(Final\ Test) - ln(Baseline\ Test)$$

which can also be expressed as $$c = ln(Final/Baseline).$$

That is, c is the log-ratio of the parameter between the final and baseline visits.

The mean percentage change between the final and baseline visit can be obtained through anti-log transformation as:

$$\%\ change = [exp(c) - 1] * 100$$

where $$c = mean\ [log(Final) - log(Baseline)]$$

The statistical assessments of between treatment group difference in changes from baseline to final visit for the total exercise time, LVEF, norepinephrine, body weight and ECG parameters were performed by a three-way analysis of variance (ANOVA):

$$Change_{ijkl} = M + T_i + C_j + B_k + B^*T_{ik} + E_{ijkl}$$

where:

$Change_{ijkl}$ is the change for the Ith patient with the ith treatment and the kth background ACE inhibitor at center j M is the overall mean $T_i$ is the ith treatment group, i=1(amlodipine), 2(placebo)

$C_j$ is the fixed center effect, j=1 to 14

$B_k$ is the background ACE inhibitor therapy, k=(ACE, 2(No ACE)

$B^*T_{ik}$ is the treatment and background ACE inhibitor therapy interaction term $E_{ijkl}$ represents the random error and E is normally distributed N(0,d).

The statistical assessments of between treatment group difference in changes from baseline to final visit for each background therapy groups were performed by a two-way analysis of variance (ANOVA):

$$Change_{ijk} = M + T_i + C_j + E_{ijk}$$

where:

$Change_{ijk}$ is the change for the kth patient with ith treatment at center j

M is the overall mean $T_i$ is the ith treatment group, i=1(amlodipine), 2(placebo)

$C_j$ is the fixed center effect, j=1 to 14

$E_{ijk}$ represents the random error and E is normally distributed N(0,d).

Treatment effects were based on the ANOVA model using Type III Sum of Squares to derive F-statistics and Least Squares Estimates (LSE). A 95% confidence interval was derived from the LSE which had a t-distribution with degrees of freedom equal to those of the error Sums of Squares of the ANOVA model. Two-tailed tests were performed on all parameters.

To compare the average effect between amlodipine and the effect of placebo, a Least Square Estimate (LSE) based on the above above three-way ANOVA model was used. The LSE for this difference was obtained by the ESTIMATE option in SAS GLM procedure.

The SAS procedure FREQ with the RANK option was used to perform a Cochran-Mantel-Hanszel test for the investigator's global evaluation, and endpoint to baseline change in NYHA class, dyspnea, nocturnal dyspnea, orthopnea, fatigue and edema.

VI. Baseline Patient Characteristics

A total of 19 female and 99 male patients participated in this study. Both treatment groups were balanced with respect to age, body weight, race, and NYHA class (i.e., Class II and III). Duration of CHF in the amlodipine group was 34 months, and 26 months in the placebo group.

About half of the patients in each group had a history of old myocardial infarction and/or angina pectoris, and symptoms of chronic ischemic heart disease. A significant number also had conduction disorders of the heart and diabetes mellitus. As a whole, the two groups of patients were comparable in terms of the profile and severity of baseline disease.

The majority of patients were on cardiac glycosides (amlodipine 48, placebo 51) and loop diuretics (amlodipine 44, placebo 50). There was no clinically important changes in the use of or dosages of these drugs during the study. Out of 118 patients, 79 (38 amlodipine, 41 placebo) patients were also taking converting enzyme inhibitors. The two treatment groups were also well balanced within the subsets of patients receiving or not receiving ACE inhibitors.

VII. Drug Administration

Medication was dispensed in identically matching amlodipine and placebo tablets with individually coded bottles prepared for each patient.

The patients received amlodipine or placebo in a single tablet q.d. Double-blind medication was taken in the morning for a period of 8 weeks. Clinical deterioration, with objective evidence of fluid retention, was treated by an increase in furosemide dosage or other diuretics as needed.

Patients were instructed to take 1 tablet each morning except on the morning of a study visit; patients came to the visit undosed. After all study parameters were completed the study medication was dispensed from a new bottle.

The duration (range) of treatment for amlodipine was 50.2 (10–71) days and 50.9 (5–74) days for placebo.

VIII. Results

A. Efficacy

Exercise Performance: Exercise performance was one of the primary end points to be analyzed in this study. Prior to randomization, potential subjects were required to participate in two exercise tests and the total exercise time had to be within 15% of one another. All exercise tests were to be conducted at same time of the day, 0.5–4 hours after dosing and at least 2 hours after a light meal. Termination of the exercise was based only on dyspnea and/or fatigue (not chest pain or ST segment depression). Exercise time was assessed three times prior to randomization and after 4 and 8 weeks of double-blind treatment.

After 8 weeks of therapy, there was a greater increase in exercise time in the amlodipine group than in the placebo group. This increase was statistically significant in both evaluable patient analysis ($p=0.02$) and intent to treat analysis ($p=0.019$). In the amlodipine intent-to-treat group, the increase in exercise time was 74 seconds (14.5%) as compared to 17 seconds (3.0%) in the placebo group.

In the above analysis of exercise time, a comparison was based on the mean exercise time of two baseline exercise tests. To minimize a "learning" effect of exercise, the data was also analyzed using only the last baseline exercise test. After 8 weeks of therapy, there was a greater ($p=0.0354$) increase in exercise time in the amlodipine intent-to-treat group as compared to the placebo group.

In the case of clinical deterioration the protocol allowed an adjustment of diuretic dosing. Thus, it can be speculated that an improvement in exercise time after amlodipine was related to the increase in diuretic therapy. This possibility was examined but failed to establish the relationship between the increase in diuretic therapy and the improvement in exercise time.

Investigator's Rating: At the end of the study, the investigator's global assessment showed that more patients improved ($p<0.027$) on amlodipine (31/56, 55%) than on placebo (17/58, 29%).

The percent of improvement in the ACE inhibitor group was 57% (17/37) in amlodipine; 33% (13/39) in placebo. The percent of patients improving was smaller for the group with no ACE inhibitors: 53% (10/19) in amlodipine and 21% (4/19) in placebo.

Left Ventricular Ejection Fraction (LVEF): Treatment with amlodipine did not affect LVEF in the trial as a whole. However, LVEF tended to increase with amlodipine in patients treated with converting enzyme inhibitors, but not in the smaller group of patients who did not receive ACE inhibitors.

Plasma Norepinephrine: Plasma norepinephrine decreased in patients treated with amlodipine (358 to 263 pg/ml), but increased on placebo (365 to 439 pg/ml, amlodipine vs placebo, $p=0.018$). Similar quantitative changes were observed in the group receiving ACE inhibitors as well as in group not receiving ACE inhibitors.

Body Weight: At the end of the study, there were no significant differences in body weight between the amlodipine and placebo groups and amlodipine and placebo groups when analyzed by the presence of edema.

Peripheral Edema: Two percent (2%) of patients in the amlodipine group and 3% in the placebo group showed an improvement in peripheral edema. Seventy-four percent (74%) of patients in the amlodipine group and 84% of patients in the placebo group showed on change in peripheral edema. Twenty-four percent (24%) of the amlodipine treated patients and 13% of the placebo patients showed a deterioration of edema. These differences were not statistically significant.

Patients Clinical Symptoms: The table below summarizes the changes in NYHA class, dyspnea, nocturnal dyspnea, and fatigue during therapy. In all of these indices, an improvement was detected with amlodipine treatment as compared to placebo. An improvement in nocturnal dyspnea and fatigue observed after amlodipine therapy approached a statistical significance (p=0.06).

| Parameters | Group | Number of Patients Who | | | Total No. Pts. | P Value Baseline vs. 8 weeks |
|---|---|---|---|---|---|---|
| | | Improved | Had No Change | Worsened | | |
| NYHA Class | Amlodipine | 12 | 33 | 3 | 48 | 0.229 |
| | Placebo | 10 | 31 | 8 | 49 | |
| Dyspnea | Amlodipine | 15 | 28 | 9 | 52 | 0.318 |
| | Placebo | 13 | 29 | 15 | 57 | |
| Nocturnal | Amlodipine | 6 | 43 | 4 | 53 | 0.06 |
| Dyspnea | Placebo | 3 | 45 | 9 | 57 | |
| Orthopnea | Amlodipine | 6 | 43 | 4 | 53 | 0.205 |
| | Placebo | 10 | 45 | 1 | 56 | |
| Fatigue | Amlodipine | 23 | 23 | 7 | 53 | 0.06 |
| | Placebo | 15 | 29 | 12 | 56 | |

Patients Quality of Life Questionnaire: Patient self assessment was made on study weeks 2, 6 and 10 which consisted of 15 questions. These questions were converted into seven (7) CHF-QOL scales including dyspnea, fatigue, affect, locus of control, sleep, life satisfaction, and total evaluation of quality of life. The results indicate that treatment effects were in favor of amlodipine for those symptoms—specific scales most related to disease activity. Patients receiving amlodipine reported an improvement in dyspnea and fatigue. This improvement was statistically significant ($p<0.01$). All changes in quality of life assessment were in favor of amlodipine, and the total score p-value was equal to 0.06. The table below summarizes the key efficacy and safety parameters which showed an improvement or favorable trend in amlodipine treated (intent-to-treat analysis) patients as compared to the placebo group.

| | Amlodipine | Placebo |
|---|---|---|
| Mean Increase in Exercise Time in sec: (N = 50 amlodipine, 54 placebo) | 73.7 (14.5%) | 17.3 (3.0%) |
| Investigators Global Assessment: | | |
| Worsening | 10 | 10 |
| No Change | 15 | 31 |
| Improvement | 31 | 17 |
| Increase in LV Ejection Fraction (%): (N = 47 for amlodipine and placebo) | 2.8 (11.5%) | 1.8 (6.9%) |

Conclusions

In this double-blind study, the clinical safety and efficacy of amlodipine was evaluated in 118 patients with heart failure. All patients had NYHA class II or III symptoms, left ventricular ejection fraction less than 40%, and the majority were treated with digoxin and diuretics. The analysis of data revealed that after 8 weeks of double-blind therapy, exercise time was significantly increased in the amlodipine treated group as compared to the placebo group. In addition, more patients treated with amlodipine experienced an improvement in CHF (NYHA class & related symptoms). Although amlodipine did not affect left ventricular ejection fraction, this particular variable tended to increase with amlodipine in patients treated with converting enzyme inhibitors. In patients treated with amlodipine, plasma norepinephrine significantly decreased, and significantly increased in the placebo group. Furthermore, as detected by a quality of life questionnaire, patients treated with amlodipine had a statistically significant improvement in both dyspnea and fatigue.

This study showed that in patients with class II-III CHF, amlodipine therapy increased exercise time, improved symptoms, and had no effect on ejection fraction in patients treated with or without ACE inhibitors.

We claim:

1. A method of treating congestive heart failure in a human subject having such condition which comprises orally administering to said human subject a congestive heart failure treating amount of amlodipine as a pharmaceutically acceptable acid addition salt thereof.

2. The method of claim 1, wherein the daily dosage is in unit dosage form of 10 mg.

3. The method of claim 2, wherein the daily dosage is given once a day.

* * * * *

UNITED STATES PATENT AND TRADEMARK OFFICE
CERTIFICATE OF CORRECTION

PATENT NO. : 5,155,120

DATED : October 13, 1992

INVENTOR(S) : Jeffrey D. Lazar, et al.

It is certified that error appears in the above-identified patent and that said Letters Patent is hereby corrected as shown below:

Column 5, line 22 "nal and clinical dyspnea and edema) signs" should read --nal dyspnea and edema) and clinical signs--; and Claim 1, column 10, line 45, "as" should read --or--.

Signed and Sealed this

Second Day of June, 1998

*Attest:*

BRUCE LEHMAN

*Attesting Officer*     *Commissioner of Patents and Trademarks*